United States Patent [19]

Harano et al.

[11] Patent Number: 5,554,790
[45] Date of Patent: Sep. 10, 1996

[54] PROCESS FOR PRODUCING ACETIC ANHYDRIDE AND ACETIC ACID

[75] Inventors: Yoshiyuki Harano; Yoshiaki Morimoto, both of Hyogo, Japan

[73] Assignee: Daicel Chemical Industries, Ltd., Osaka, Japan

[21] Appl. No.: 408,703

[22] Filed: Mar. 22, 1995

[30] Foreign Application Priority Data

Apr. 4, 1994 [JP] Japan .................................. 6-066319

[51] Int. Cl.$^6$ ........................... C07C 51/12; C07C 45/49
[52] U.S. Cl. ........................ 562/519; 562/608; 562/577; 568/484; 568/492; 568/487; 568/491
[58] Field of Search ..................... 562/519, 608, 562/577; 568/484, 492, 487, 491

[56] References Cited

U.S. PATENT DOCUMENTS 5,380,929  1/1995  Erpenbach et al. ..................... 562/519

FOREIGN PATENT DOCUMENTS

| 350635 | 1/1990 | European Pat. Off. . |
| 61-58803 | 3/1986 | Japan . |
| 2-104551 | 4/1990 | Japan . |
| 1063133 | 7/1964 | United Kingdom . |

OTHER PUBLICATIONS

Adv. Chem. Ser., 230, pp. 377–394 (1992).

*Primary Examiner*—Gary Geist
*Assistant Examiner*—Rosalynd A. Williams
*Attorney, Agent, or Firm*—Flynn, Thiel, Boutell & Tanis, P.C.

[57] ABSTRACT

In a process for producing acetic anhydride and acetic acid by reacting methanol and methyl acetate, optionally together with dimethyl ether, with carbon monoxide, acetic anhydride and acetic acid are effectively produced with the use of a sequence of production facilities by carrying out separation of low-boiling point fraction mainly consisting of methyl iodide, methyl acetate and dimethyl ether with the use of at least two distillation zones, separating catalyst drops entrained from the vapor-liquid separation zone in at least one distillation zone and further by controlling the pressurization of the vapor-liquid separation zone and the above distillation zones under 5 bar to a pressure greater than atmospheric pressure. The invention not only reduces the facility cost and the energy cost to be borne for separation, but also improves the capability of recovering low-boiling point fractions and further recovers the entrained catalyst, so that acetic anhydride and acetic acid can efficiently be produced with the use of a sequence of production facilities.

14 Claims, No Drawings

PROCESS FOR PRODUCING ACETIC ANHYDRIDE AND ACETIC ACID

FIELD OF INDUSTRIAL APPLICATION

The present invention relates to a process for producing acetic anhydride and acetic acid from methanol and methyl acetate, optionally together with dimethyl ether, with the use of a sequence of continuous production facilities.

PRIOR ART

Acetic acid is a fundamental compound employed in large quantity as a starting material of acetic esters, acetic anhydride, vinyl acetate and terephthalic acid and demanded in a wide spectrum of industries, such as polymer and other chemical industries. On the other hand, acetic arthydride is a compound not only employed in large quantities as a raw material for producing cellulose acetate but also is useful as a raw material of chemical products such as drugs, perfumes and dyes. The above acetic acid and acetic anhydride are chemical compounds interrelated in practical use. For example, in the cellulose acetate industry, acetic anhydride is produced from acetic acid, and reacted with cellulose to thereby obtain cellulose acetate and acetic acid, the latter being recycled.

A process for obtaining acetic acid and acetic anhydride is known, in which both are produced by reacting either methyl acetate and methanol or dimethyl ether and methanol with carbon monoxide, using a continuous series of facilities.

For example, JP-A 2-104,551, corresponding to AU-A 89 38037 published on Jan. 18, 1990, shows a process for separating and purifying acetic acid and acetic anhydride obtained in such a reaction zone. More specifically, the catalyst solution is separated with the use of a two-stage vapor-liquid separation zone having pressures different in each stage while the carbonylation product is separated from the low-boiling point raw materials at atmospheric pressure in a one-stage distillation zone. The above shown processes not only require a two-stage vapor-liquid separation zone for circulating the catalyst solution to the reactor, but also have a drawback in that the second vapor-liquid separation zone is controlled under a reduced pressure, so that the catalyst becomes unstable and crystallizes. Further, it becomes necessary to increase the pressure of the fraction evaporated from the second vapor-liquid separation zone at a reduced pressure, prior to feeding same to the distillation zone. Still further, in the process described in the above laid-open specifications, the controlled pressure of the distillation zone where the product acetic acid and acetic anhydride are separated from low-boiling point fractions such as methyl iodide, methyl acetate and dimethyl ether is at atmospheric pressure, so that the capacity of cooling recovery of the low-boiling point fractions such as methyl iodide, methyl acetate and dimethyl ether is poor at the top of the distillation column. Thus, problems are pointed out such that the heat exchanger to be disposed at the top of the distillation column must be huge, that the amount of energy consumed by cooling is increased, and that the facility for recovery of an offgas discharged from the top of the distillation column must be huge.

Further, there is a problem that it is of no avail from the economic point of view when the employed catalyst is expensive because, in the distillation zone, the catalyst entrained from the vapor-liquid separation zone is not recovered.

DESCRIPTION OF THE INVENTION

The object of the present invention is to provide a process for producing acetic acid and acetic anhydride, recovering low boiling point fractions such as methyl iodide, methyl acetate and dimethyl ether and entrained drops of the catalyst from the vapor-liquid separation zone effectively in the production of acetic acid and acetic anhydride with a series of continuous production facilities.

The purpose of the invention is to solve the above shown defects. The process of the invention produces acetic anhydride and acetic acid by reacting methanol and methyl acetate, optionally together with dimethyl ether, with carbon monoxide, and comprises a reaction zone, a vapor-liquid separation zone, at least two distillation zones, and a third distillation (purification) zone.

The low boiling point fraction is mainly composed of methyl iodide, methyl acetate and dimethyl ether and can be effectively separated in at least two distillation zones. The catalyst in the form of drops entrained from the vapor-liquid separation zone can be separated in at least one distillation zone and returned to the reaction zone and/or the vapor-liquid separation zone.

The invention includes a practically preferable embodiment comprising carrying out separation of three components, i.e, the low-boiling point fraction consisting mainly of methyl iodide, methyl acetate and dimethyl ether, the catalyst entrained from the vapor-liquid separation zone and the product acetic anhydride and acetic acid, with the use of at least two distillation zones.

It is preferable that the steps of the vapor-liquid separation zone and the distillation zones can be effected by adjusting the pressure at 5 bar or below, that is, 5 bar to a pressure higher than atmospheric pressure.

That is, according to the present invention, there is provided a process for producing acetic anhydride and acetic acid by reacting methanol and methyl acetate, optionally together with dimethyl ether, with carbon monoxide, which comprises the steps of:

(a) reacting methanol and methyl acetate, optionally together with dimethyl ether, with carbon monoxide or a mixture of carbon monoxide and hydrogen in the presence of a catalyst in a reaction zone at 150° to 250° C. and at 5 to 120 bar;

(b) flash-evaporating a carbonylated mixture withdrawn from the reaction zone in a vapor-liquid separation zone at 5 bar to a pressure higher than atmospheric pressure to thereby evaporate a major proportion of volatile fractions, which are fed to the first distillation zone, and recycling a catalyst solution not evaporated in the vapor-liquid separation zone to the reaction zone;

(c) obtaining in the first distillation zone a low-boiling point fraction from the column top part and recycling the same to the reaction zone, and simultaneously obtaining a high-boiling point fraction containing part of the catalyst mixed in by, for example, entrainment from the column bottom part and recycling the same to the reaction zone and/or the vapor-liquid separation zone, while obtaining as a sidestream a mid-boiling point fraction containing mainly acetic anhydride and acetic acid;

(d) feeding the mid-boiling point fraction containing mainly acetic anhydride and acetic acid, obtained as the sidestream in the first distillation zone, to the second distillation zone;

(e) further, obtaining in the second distillation zone a remaining low-boiling point fraction from the column top part and recycling the same to the reaction zone;

(f) either obtaining a fraction consisting mainly of acetic anhydride and acetic acid as a sidestream or from the column bottom part and feeding the same to the third distillation zone, or obtaining a high-boiling point fraction containing part of the catalyst mixed in by, for example, entrainment from the column bottom part and recycling the same to the reaction zone and/or the vapor-liquid separation zone while obtaining as a sidestream a fraction consisting mainly of acetic anhydride and acetic acid and feeding the same to the third distillation zone; and (g) obtaining in the third distillation zone acetic acid from the column top part and obtaining acetic anhydride as a sidestream or from the column bottom part.

The metals of Group VIII of the periodic table, as well as methyl iodide, may be used as the catalyst in the above reaction. Examples of these metals include palladium, iridium, rhodium, nickel and cobalt. Of them, rhodium and nickel are preferred. Rhodium exhibits the highest activity. Although the morphology of the catalyst in use is not particularly limited, it is preferred that the catalyst be dissolved under reaction conditions, and it is especially preferred that the catalyst be one forming a carbonyl complex species in the reaction system.

Although the alkali metal salt used as a promoter is not particularly limited as long as it can be dissolved under reaction conditions, iodide and acetate salts are preferred. In particular, lithium, sodium and potassium iodides and lithium, sodium and potassium acetates are especially preferred. Also, salts of the elements having Lewis acidities of Group III of the periodic table may be used as the promoter. Although the morphology of each salt is not particularly limited, as long as it is soluble under reaction conditions, iodide and acetate salts are preferred. In particular, aluminum and boron iodides and acetates, aluminum chloride, boric acid and metaboric acid are especially preferred.

The process of the present invention in which rhodium is used as an example of the catalysts will be described below.

The concentration of rhodium in a reaction fluid is generally in the range of 100 to 10,000 ppm, preferably 300 to 3000 ppm. The concentrations of methyl iodide, methyl acetate and/or dimethyl ether, acetic anhydride, and acetic acid in the reaction fluid are generally in the ranges of 10 to 30%, 5 to 40%, 10 to 40%, 4, and 0 to 40% by weight, respectively. The concentrations of methanol, methyl acetate and dimethyl ether are changeable on occasion, depending on the ratio of produced acetic anhydride to acetic acid. Also, water may be fed as the raw material. Although the rate-determining step of this reaction when the concentrations of the promoter and methyl acetate are high is the reaction between rhodium and methyl iodide, when rhodium and methyl iodide are in high concentration ranges, the practical reaction rate is the reaction between the iodide as the promoter and methyl acetate, as described Adv. Chem. Ser, 230, 377–394 (1992).

The carbon monoxide used in the reaction is not necessarily pure. The presence of an extremely small amount of an inert-gas such as carbon dioxide, nitrogen or methane never interferes with the carbonylation, as long as the partial pressure of carbon monoxide in the reactor is held at a constant value. Although the hydrogen content advantageously acts on the catalytic activity, it may lower the process selectivity by the formation of a hydrogenation product such as ethylidene diacetate. Accordingly, the partial pressure of hydrogen in the reactor is preferred to range from 0 to 10 atm.

In the reactor, the reaction pressure, the reaction temperature and the partial pressure of carbon monoxide are held at 5 to 120 bar, 150 to 250° C. and 5 to 70 atm, respectively.

The crude reaction fluid obtained by tile reaction in the presence of the catalyst and promoter is withdrawn from the reactor, and is flash-evaporated in a vapor-liquid separation zone controlled under a pressure not higher than the reaction pressure to thereby separate the same into an unevaporated catalyst solution to be recycled and a vapor containing produced acetic acid and acetic anhydride. Although the pressure of the vapor-liquid separation zone is not particularly limited as long as it is not higher than the pressure of the reaction zone, only a slight difference therebetween is disadvantageous from the viewpoint of the efficiency of the process because the amount of vapor generated by the flash evaporation is small and the amount of recycled catalyst solution is large. For example, heating of the vapor-liquid separation zone in the presence or absence of CO and $H_2$ would be considered as means for increasing the amount of generated vapor. However, the above heating causes a problem such that the catalyst becomes unstable in the vapor-liquid separation zone to thereby crystallize. Moreover, the heating of the vapor-liquid separation zone in the presence of CO and $H_2$ causes not only a problem such that CO and $H_2$ are additionally required but also a problem such that, for example, the low-boiling point raw materials are entrained by fed CO and $H_2$ gases from the distillation zone to result in the loss thereof, the recovery facility for which is inevitably huge. Contrarily, when the difference in pressure between the vapor-liquid separation zone and the reaction zone is large, there are problems such that not only is the vapor compelled to have a pressure increase prior to the feed to the distillation zone following the vapor-liquid separation zone because of the relative lowness of the pressure of the vapor-liquid separation zone, but also the catalyst is unstable in the vapor-liquid separation zone to thereby crystallize. Therefore, it is preferred that the pressure of the vapor-liquid separation zone be controlled under 5 bar to a pressure higher than the atmospheric pressure, especially 4 bar or below and 1.5 bar or above. According to necessity, CO and/or $H_2$ gas may be introduced thereinto.

The unevaporated catalyst solution separated in the vapor-liquid separation zone is recycled as it is or after some treatment to the reaction zone. High-boiling point impurities such as tar and ethylidene diacetate are contained in the catalyst solution not evaporated in the vapor-liquid separation zone. Therefore, according to necessity, the impurities may be decomposed and removed or just separated for purification prior to the recycling of the catalyst solution. In the recycling of the unevaporated catalyst solution separated in the vapor-liquid separation zone after the treatment of decomposition and removal or separation for purification to the reaction zone, either the whole or only part of the catalyst solution may be subjected to the above treatment.

The vapor generated by the flash evaporation in the vapor-liquid separation zone and containing acetic acid and acetic anhydride is fed to the first distillation zone. When the controlled pressure of the first distillation zone is higher than that of the vapor-liquid separation zone, not only must the pressure of the vapor be increased prior to the feed from the vapor-liquid separation zone to the first distillation zone, but also the cost of the facilities of the first distillation zone per se and the energy cost to be borne for the separation rise, thereby causing disadvantages in the process. Contrarily, when the controlled pressure of the first distillation zone is too low, the capacity of cooling recovery of methyl iodide, methyl acetate and dimethyl ether is lowered at the top part of the distillation column. This causes problems such that the heat exchanger to be disposed at the top part of the distillation column must be huge, that the amount of energy consumed by cooling is increased, that the facility for recovery of an offgas discharged from the top part of the distillation column must be huge, and that the entrained catalyst becomes unstable and crystallizes in the distillation column therefore, it is preferred that the pressure of the first distillation zone be controlled under 5 bar to a pressure higher than atmospheric pressure, especially 4 bar or below and 1.5 bar or above. It is preferable that the pressure of the vapor-liquid separation zone (A zone) is the same as or a little higher than that of the first distillation zone (B zone).

The vapor fed from the vapor-liquid separation zone to the distillation zone contains not only low-boiling point fractions such as methyl iodide, methyl acetate and dimethyl ether and acetic acid and acetic anhydride as products, but also part of the catalyst mixed in because of the entrainment from the vapor-liquid separation zone. Attempting complete separation of three components, i.e, the low-boiling point fraction vapor composed of methyl iodide, methyl acetate and dimethyl ether, the catalyst mixed in because of entrainment from the vapor-liquid separation zone and acetic acid and acetic anhydride as products, only with the use of one distillation zone, causes problems such that the size (number of plates, column diameter and column height) of the distillation column to be provided for the separation and the energy to be supplied for the separation are impracticably huge. Therefore, it is preferred that at least two distillation zones be employed in the separation of acetic acid and acetic anhydride as products from the low-boiling point fraction vapor of methyl iodide, methyl acetate and dimethyl ether fed from the vapor-liquid separation zone to the distillation zone.

The vapor fed from the vapor-liquid separation zone to the distillation zone contains part of the catalyst mixed in because of entrainment, etc. Accordingly, in the first distillation zone, it is preferred to obtain a high-boiling point fraction containing part of the catalyst mixed in because of entrainment, etc, from the column bottom part and to obtain a mid-boiling point fraction containing mainly acetic acid and acetic anhydride as a sidestream. Although in this step the sidestream cut of the mid-boiling point fraction containing mainly acetic acid and acetic anhydride may be in the form of a liquid or a vapor, it is preferred that the sidestream cut be in the form of a vapor.

The low-boiling point fraction obtained from the column top part in the first distillation zone and composed mainly of methyl iodide and methyl acetate is recycled to the reaction zone. The mid-boiling point fraction containing mainly acetic acid and acetic arthydride and obtained as the sidestream in the first distillation zone is fed to the second distillation zone. The high-boiling point fraction containing part of the catalyst mixed in because of the entrainment, etc, and obtained from the column bottom part in the first distillation zone is recycled to the reaction zone and/or the vapor-liquid separation zone.

In the fractional distillation in the first distillation zone, an off,as consisting mainly of $CO_2$, CO, $CH_4$ and $N_2$ is withdrawn from the column top part, washed with methanol, methyl acetate and/or dimethyl ether as a feed material to thereby remove remaining methyl iodide, and fed to combustion, while a mixture containing at least one member selected from among methanol, methyl acetate and dimethyl ether may be fed to the reaction zone. The above washing of the offgas may be conducted by the conventional method as described in, for example, Japanese Patent Laid-Open No. 58803/1986.

The fraction obtained as the sidestream in the first distillation zone, which contains large amounts of acetic acid and acetic anhydride together with minute amounts of methyl iodide and methyl acetate, is fed to the second distillation zone. In the second distillation zone, a low-boiling point fraction composed mainly of methyl iodide and methyl acetate is obtained from the column top part, while a fraction containing mainly acetic acid and acetic anhydride is obtained as a sidestream or from the column bottom part. When a high-boiling point fraction containing part of the catalyst mixed in because of the entrainment, etc, remains, the low-boiling point fraction composed mainly of methyl iodide and methyl acetate is obtained from the column top part, the fraction containing mainly acetic acid and acetic anhydride is obtained as the sidestream, and the high-boiling point fraction containing part of the catalyst is obtained from the column bottom part. The high-boiling point fraction is recycled to the reaction zone and/or the vapor-liquid separation zone. Although the above sidestream may be in the form of a liquid or a vapor, it is preferred to be in the form of a vapor. In this step, when the controlled pressure of the second distillation zone is higher than that of the first distillation zone, not only must the pressure of the fraction be increased prior to the feed from the first distillation zone to the second distillation zone, but also the cost of the facilities of the second distillation zone per se and the energy cost to be borne for the separation rise, thereby causing disadvantages in the process. Contrarily, when the controlled pressure of the second distillation zone is too low, the capacity of cooling recovery of methyl iodide, methyl acetate and dimethyl ether is lowered at the top part of the distillation column. This causes problems such that the heat exchanger to be disposed at the top part of the distillation column must be huge, that the amount of energy consumed by cooling is increased, and that the entrained catalyst becomes unstable and crystallizes in the distillation column. Therefore, it is preferred that the pressure of the second distillation zone be controlled under 5 bar to a pressure higher larger than atmospheric pressure, especially 4 bar or below and 1.5 bar or above.

If desired, in the fractional distillation in the second distillation zone, an offgas consisting mainly of $CO_2$, CO, $CH_4$ and $N_2$ may be withdrawn from the column top part, washed with methanol, methyl acetate and/or dimethyl ether as a feed material to thereby remove remaining methyl iodide, and fed to combustion, while a mixture containing at least one member selected from among methanol, methyl acetate and dimethyl ether may be fed to the reaction zone. In this step, the washing of the offgas withdrawn from the second distillation zone may be conducted by the use of the above facilities employed in the washing of the offgas in the first distillation zone.

The fraction containing mainly acetic acid and acetic anhydride and obtained as a sidestream or from the column bottom part in the second distillation zone is fed to the third distillation zone. In the third distillation zone, a fraction composed mainly of acetic acid is obtained from the column top part, while a fraction composed mainly of acetic anhydride is obtained as a sidestream or from the column bottom part.

In this step, the controlled pressure of the third distillation zone is not particularly limited. However, when the controlled pressure of the third distillation zone is higher than that of the second distillation zone, not only must the pressure of the fraction be increased prior to the feed from the second distillation zone to the third distillation zone, but also the cost of the facilities of the third distillation zone per se and the energy cost to be borne for the separation rise, thereby causing disadvantages in the process. Therefore, it is preferred that the controlled pressure of the third distillation zone be 5 bar or below, especially 1 bar or below.

When a sidestream is taken in the third distillation zone, the sidestream composed of a fraction containing acetic anhydride may be in the form of a liquid or a vapor, although the latter is preferred.

According to necessity, separating and treating steps may be provided prior to the feed to the third distillation zone in order to remove a minute amount of impurities from the fraction composed of acetic acid and acetic anhydride and obtained from the second distillation zone.

The acetic acid obtained from the column top part in the third distillation zone as it is may be either recovered as a product, or recycled to the reaction. Moreover, according to necessity, at least one operation selected from among ozonization, treatment with an ion exchange resin and further distillation purification may be carried out, or at least two operations selected therefrom may be performed in combination before the recovery of the acetic acid as a product. Likewise, the acetic anhydride obtained as the sidestream or from the column bottom part in the third distillation zone may be recovered as a product, and according to necessity, at least one operation selected from among ozonization, treatment with an ion exchange resin and further distillation purification may be carried out, or at least two operations selected therefrom may be performed in combination before the recovery of the acetic anhydride as a product.

The present invention not only reduces the facility cost and the energy cost to be borne for the separation, but also improves the capability of recovering low-boiling point fractions and further recovers the entrained catalyst, so that acetic anhydride and acetic acid can efficiently be produced with the use of a sequence of production facilities according to the present invention.

EXAMPLES

Hereinbelow, the present invention will be described in greater detail with reference to the Examples, which should not be construed as limiting the scope of the invention.

EXAMPLE 1

Acetic acid and acetic anhydride were each produced at an hourly rate of 0.1 kg with the use of a pilot plant for producing acetic anhydride and acetic acid, which was equipped with a reaction zone (reactor) of 500 ml in inner volume. The reaction fluid contained rhodium, methyl iodide and methyl acetate in respective concentrations of 1000 ppm, 204 by weight and 174 by weight. As a promoter for accelerating the reaction, aluminum acetate, lithium iodide and boric acid were added in respective amounts of 10 times, 20 times and 20 times the mol of the rhodium. The reaction was carried out at 190° C. and at 30 kg/cm$^2$. The reaction fluid was transferred to a vapor-liquid separation zone (evaporator) controlled under a pressure of 1.4 KG (2.4 kg/cm$^2$) to thereby effect flash evaporation. The liquid fraction containing the catalyst which was not evaporated by the flash evaporation was recycled to the reactor.

The vapor generated by the flash evaporation in the evaporator was fed to the first distillation zone (distillation column). The first distillation column was controlled under a pressure of 1.4 KG (2.4 kg/cm$^2$) and a reflux ratio of 3.5. In the first distillation column, a low-boiling point fraction composed mainly of methyl iodide and methyl acetate was obtained from the top part of the column, and recycled to the reactor. Simultaneously, a mid-boiling point fraction containing mainly acetic acid and acetic anhydride was obtained as a sidestream, while a high-boiling point fraction containing part of the catalyst mixed in because of the entrainment, etc, was obtained from the bottom part of the column. The mid-boiling point fraction containing mainly acetic acid and acetic anhydride and obtained as the sidestream from the first distillation column was fed to the second distillation zone (distillation column), while the high-boiling point fraction fluid obtained from the bottom part of the first distillation column was recycled to the reactor.

An offgas consisting mainly of $CO_2$, CO, $CH_4$ and $N_2$ was withdrawn via a heat exchanger from the top part of the first distillation column, washed with methanol and methyl acetate to thereby remove remaining methyl iodide, and fed to combustion, while a mixture of methanol and methyl acetate containing part of the offgas and methyl iodide was recycled to the reaction zone. The second distillation column was controlled at a pressure of 1.4 KG (2.4 kg/cm$^2$) and a reflux ratio of 2.3. In the second distillation column, a low-boiling point fraction composed mainly of methyl iodide and methyl acetate was obtained from the top part of the column, and recycled to the reactor. Simultaneously, a fluid fraction composed mainly of acetic acid and acetic anhydride was obtained as a sidestream and fed to the third distillation zone (distillation column), while a high-boiling point fraction fluid obtained from the column bottom part of the second distillation zone was recycled to the reaction step.

The third distillation column was controlled at a pressure of 300 Torr and a reflux ratio of 5.0. In the third distillation column, acetic acid as a desired product was obtained from the top part, while a fraction composed mainly of acetic anhydride was obtained from the bottom part. The low-boiling point and high-boiling point fractions were removed from the fraction composed mainly of acetic anhydride and obtained from the bottom part of the third distillation column, thereby obtaining acetic anhydride as a desired product.

EXAMPLE 2

Acetic acid and acetic anhydride were each produced at an hourly rate of 0.2 kg with the use of a pilot plant for producing acetic anhydride and acetic acid, which was equipped with a reaction zone (reactor) of 500 ml in inner volume. The reaction fluid contained rhodium, methyl iodide and methyl acetate in respective concentrations of 1000 ppm, 204 by weight and 174 by weight. As a promoter for accelerating the reaction, aluminum acetate, lithium iodide and boric acid were added in respective amounts of 10 times, 20 times and 20 times the mol of the rhodium. The reaction was carried out at 190° C. and at 29.4 bar. The reaction fluid was transferred to a vapor-liquid separation zone (evaporator) controlled at a pressure of 2.4 bar to thereby effect flash evaporation. The liquid fraction containing the catalyst which was not evaporated by the flash evaporation was recycled to the reactor.

The vapor generated by the flash evaporation in the evaporator was once cooled and freed from pressure, liquefied again and fed with a pump to the 20th from the top plate of the first distillation zone (distillation column) as the oldershow distillation column having 40 mm diameter and 20 plates. The composition of the liquid to the first distillation was 37.2 wt % of methyl iodide, 25.3 wt % of methyl acetate, 17.3 wt % of acetic acid, 18.5 wt % of acetic anhydride and 1.7 wt % of others. The first distillation column was controlled at a pressure of 2.4 bar and a reflux ratio of 3.5. In the first distillation column, a low-boiling point fraction composed mainly of methyl iodide and methyl acetate was obtained from the top part of the column at a distillate rate of 45 %, and recycled to the reactor. Simultaneously, a mid-boiling point fraction containing mainly acetic acid and acetic anhydride was obtained as a sidestream with the sidestream rate of 52%, while a high-boiling point fraction containing part of the catalyst mixed in because of entrainment, etc, was obtained from the bottom part of the column. The composition of the low-boiling point fraction obtained from the top of the first dilution column was 72.9 wt % of methyl iodide, 26.0 wt % of methyl acetate, 1.1 wt % of others. Further, the location of the sidestream is second from the bottom (when the bottom is numbered as first).

The mid-boiling point fraction containing mainly acetic acid and acetic anhydride and obtained as the sidestream from the first distillation column was fed to the second distillation zone (distillation column), while the high-boiling point fraction fluid obtained from the bottom part of the first distillation column was recycled to the reactor. The composition of the above middle-boiling point fraction was 32.0 wt % of acetic acid, 32.5 wt % of acetic anhydride, 8.1 wt % of methyl iodide, 25.8 wt % of methyl acetate and 1.6 wt % of others.

The second distillation column, an oldershow distillation column having 40 mm diameter and 30 plates, was controlled under a pressure of 2.4 bar and a reflux ratio of 2.3. Further, the preparing plate is 13th from the top. In the second distillation column, a low-boiling point fraction composed mainly of methyl iodide and methyl acetate was obtained from the top part of the column with a distillation rate of 35 %, and recycled to the reactor. Simultaneously, the middle-boiling point fraction consisting mainly of acetic acid and acetic arthydride was obtained as a sidestream with a sidestream rate of 64% and a high-boiling point fraction consisting partly of the entrained catalyst was obtained from the bottom of the column. The composition of the low-boiling point fraction obtained from the top of the second distillation column was 22.9 wt % of methyl iodide, 72.9 wt % of methyl acetate, 4.2 wt % of others. The middle-boiling point fraction consisting mainly of acetic acid and acetic anhydride and obtained from sidestream of the second distillation column was fed to the third distillation zone (distillation column), while a high-boiling point fraction fluid obtained from the column bottom part of the second distillation column was recycled to the reaction step. The composition of the middle-boiling point fraction was 49.6 wt % of acetic acid, 50.3 wt % of acetic anhydride and 0.1 wt % of others. Further, the location of the sidestream is second from the bottom (when the bottom were counted first).

The third distillation column, an oldershow distillation column having 40 mm diameter and 60 plates, was controlled at a pressure of 0.4 bar and a reflux ratio of 5.0. Further, the preparing plate was 37th from the top. In the third distillation column, acetic acid as a desired product which was 99.9 wt % was obtained from the top part, while a fraction composed 99.8 wt % of acetic anhydride and 0.1 wt % of acetic acid was obtained from the bottom part. The low-boiling point and high-boiling point fractions were removed from the fraction composed mainly of acetic anhydride and obtained from the bottom part of the third distillation column, thereby obtaining acetic anhydride as a desired product.

In pilot producing, the concentration of the rhodium in the reactor was continuously measured, it reduced at a rate of about 1 ppm/day.

Comparative Example 1

The vapor generated by the flash evaporation in the evaporator, obtained in Example 2, was cooled and freed from pressure, liquefied and fed again with a pump to the 13th plate from the top of a distillation column having 40 mm diameter and 30 plates and controlled under normal pressure and a reflux ratio of 3.5. A low-boiling point fraction consisting mainly of methyl iodide and methyl acetate was obtained from the top of the column and fed to the reactor and a liquid consisting mainly of acetic acid and acetic anhydride was obtained from the bottom of the column and provided to the third distillation column (this indicates separation of the low-boiling point fraction was conducted in one distillation zone, and further the entrained catalyst was not fed to the reactor).

The third distillation column was an oldershow distillation column having 40 mm diameter and 60 plates and controlled at a pressure 0.4 bar and a reflux ratio 5.0. In the third distillation column, the product of acetic acid was obtained from the top of the column and a fraction mainly consisting of acetic anhydride was obtained from the bottom of the column. The low-boiling point and high-boiling point fractions were removed from a fraction mainly composed of acetic anhydride and obtained from the bottom part of the third distillation column, thereby obtaining acetic arthydride as a desired product.

The concentration of rhodium in the reaction liquid reduced at a rate of about 3 ppm/day because the catalyst entrained from the vapor-liquid separation zone was not recovered.

Further, not only did the amount of methyl iodide mixed into the product of acetic acid increase but the amount of methyl iodide exhausted in gaseous form from the bend of the condenser of the first distillation column increased, the result being that the concentration of methyl iodide in the reacting liquid could not be kept constant.

What is claimed is:

1. A process for producing acetic anhydride and acetic acid by reacting methanol and methyl acetate with carbon monoxide, which comprises the steps of:

(a) reacting methanol and methyl acetate with carbon monoxide or a mixture of carbon monoxide and hydrogen in the presence of a catalyst in a reaction zone at a temperature of from 150° to 250° C. and a pressure of from 5 to 120 bar;

(b) withdrawing a carbonylated mixture from the reaction zone and flash-evaporating the carbonylated mixture in a vapor-liquid separation zone at a pressure of from above atmospheric pressure up to 5 bar to evaporate a major portion of volatile fractions contained therein, feeding the evaporated volatile fractions to a first distillation zone and recycling a catalyst solution not evaporated in the vapor-liquid separation zone to the reaction zone;

(c) conducting distillation in a column in said first distillation zone of said evaporated volatile fractions at a pressure of from above atmospheric pressure up to 5 bar to obtain a low-boiling point fraction from an upper portion of the column, a mid-boiling point fraction containing acetic anhydride and acetic acid as a sidestream from said column and a high-boiling point fraction having catalyst contained therein from a lower portion of said column, recycling the low-boiling point fraction to the reaction zone and the high-boiling point fraction to at least one of the reaction zone and the vapor-liquid separation zone;

(d) feeding the sidestream of the mid-boiling point fraction containing acetic anhydride and acetic acid to a second distillation zone;

(e) conducting distillation in a column in said second distillation zone of said sidestream of the mid-boiling point fraction containing acetic anhydride and acetic acid at a pressure of from above atmospheric pressure up to 5 bar to obtain a low-boiling point fraction from an upper portion of the column and recycling the low-boiling point fraction to the reaction zone;

(f) obtaining a sidestream of a fraction containing acetic anhydride and acetic acid and feeding it to a third distillation zone; and (g) conducting distillation in a column in said third distillation zone of the sidestream of the fraction containing acetic anhydride and acetic acid from the second distillation zone to obtain acetic acid from an upper portion of the column and acetic anhydride from a lower portion of the column.

2. The process as claimed in claim 1, wherein an offgas consisting mainly of $CO_2$, $CO$, $CH_4$ and $N_2$ is withdrawn from the column in at least one of the first and second distillation zones, washed with at least one of methanol and methyl acetate as a feed material to thereby remove remaining methyl iodide, and fed to combustion while a mixture composed of at least one of the methanol and methyl acetate is fed to the reaction zone.

3. The process as claimed in claim 1, wherein the third distillation zone is controlled under a pressure of 5 bar or below.

4. The process as claimed in claim 1, wherein the third distillation zone is controlled under a pressure of 1 bar or below.

5. The process as claimed in claim 1, wherein dimethyl ether is contained in the reaction zone.

6. The process as claimed in claim 1, wherein a high-boiling fraction having catalyst contained therein is obtained from a lower portion of the column in the second distillation zone and recycled to at least one of the reaction zone and the vapor-liquid separation zone.

7. The process as claimed in claim 1, wherein the catalyst is at least one member selected from the group consisting methyl iodide, palladium, iridium, rhodium, nickel and cobalt.

8. The process as claimed in claim 7, wherein the catalyst is at least one of rhodium and nickel.

9. The process as claimed in claim 1, wherein water is fed into the reaction zone.

10. The process as claimed in claim 1, wherein rhodium is the catalyst and is present in the reaction zone at a concentration of 100 to 10,000 ppm.

11. The process as claimed in claim 1, wherein methyl iodide is present in the reaction zone in an amount of from 10 to 30 wt %.

12. The process as claimed in claim 1, wherein methyl acetate is present in the reaction zone in an amount of from 10 to 40 wt %.

13. The process as claimed in claim 1, wherein dimethyl ether is present in the reaction zone in an amount of from 0 to 40 wt. %.

14. The process as claimed in claim 1, wherein at least one promoter selected from the group consisting of lithium iodide, sodium iodide, potassium iodide, lithium acetate, sodium acetate, potassium acetate, aluminum iodide, boron iodide, aluminum acetate, boron acetate, aluminum chloride, boric acid and metaboric acid are present in the reaction zone.

* * * * *

UNITED STATES PATENT AND TRADEMARK OFFICE
CERTIFICATE OF CORRECTION

PATENT NO. : 5,554,790
DATED : September 10, 1996
INVENTOR(S) : Yoshiyuki HARANO et al It is certified that error appears in the above-indentified patent and that said Letters Patent is hereby corrected as shown below:

Column 12, line 7; after "consisting" insert ---of---.

Signed and Sealed this

Twenty-seventh Day of May, 1997

Attest:

BRUCE LEHMAN

Attesting Officer

Commissioner of Patents and Trademarks